(12) United States Patent
Ostergard

(10) Patent No.: US 10,660,780 B1
(45) Date of Patent: May 26, 2020

(54) SHOULDER STABILIZING SYSTEM

(71) Applicant: Doak Ostergard, Lincoln, NE (US)

(72) Inventor: Doak Ostergard, Lincoln, NE (US)

( * ) Notice: Subject to any disclaimer, the term of this patent is extended or adjusted under 35 U.S.C. 154(b) by 457 days.

(21) Appl. No.: 15/807,866

(22) Filed: Nov. 9, 2017

(51) Int. Cl.
*A61F 5/01* (2006.01)
(52) U.S. Cl.
CPC .................... *A61F 5/0104* (2013.01)
(58) Field of Classification Search
CPC ........ A61F 5/01; A61F 5/0102; A61F 5/0104; A61F 5/026; A61F 2007/003; A61F 13/14; A61F 13/146; A61F 2/40; A61F 2/4612; A61F 2/581; A61G 2200/54; A61G 13/0072; A45F 3/12; A41F 15/00; A41F 15/005; A41F 15/007; A41D 27/26; A63B 21/4005
See application file for complete search history.

(56) References Cited

U.S. PATENT DOCUMENTS

| | | | | |
|---|---|---|---|---|
| 5,188,587 A | * | 2/1993 | McGuire | A61F 5/0118 128/874 |
| 5,403,268 A | * | 4/1995 | Clement | A61F 5/3738 128/DIG. 19 |
| 5,628,725 A | | 5/1997 | Ostergard | |
| 8,287,478 B2 | | 10/2012 | Ostergard et al. | |
| 10,603,201 | * | 3/2020 | Eriksson | A61F 5/3723 |
| 2015/0057588 A1 | * | 2/2015 | Eriksson | A61F 5/0118 602/20 |
| 2016/0213504 A1 | * | 7/2016 | Colleran | A61F 5/013 |

* cited by examiner

*Primary Examiner* — Tarla R Patel
(74) *Attorney, Agent, or Firm* — Dennis L. Thomte; Thomte Patent Law Office LLC

(57) ABSTRACT

A shoulder stabilizing system is provided which provides 360 degrees of support utilizing four adjustable tensioning systems that are each responsible for a quadrant of the shoulder. The four tensioning systems work together to give the user the ability to control all movements of the shoulder including internal and external rotation, horizontal abduction and adduction, while offering 360 degrees support to the shoulder capsule.

10 Claims, 7 Drawing Sheets

SHOULDER STABILIZING SYSTEM

BACKGROUND OF THE INVENTION

Field of the Invention

This invention relates to a shoulder stabilizing system which provides 360 degrees of support utilizing four adjustable tensioning systems that are each responsible for a quadrant of the shoulder. Even more particularly, the four tensioning systems work together to give the user the ability to control all movements of the shoulder including internal and external rotation, horizontal abduction and adduction, while offering 360 degrees support to the shoulder capsule.

Description of the Related Art

It is common for athletes with minor shoulder injuries to continue to participate in sports activities. A variety of devices and methods have been developed for managing shoulder injuries to reduce pain and minimize the risk of more serious injury.

It is also common for athletes to use tape to immobilize or stabilize a joint, such as the shoulder, against further injury. However, proper taping of the shoulder injury generally requires an experienced trainer or doctor. Additionally, it is difficult for an athlete to self-tape certain injuries, especially shoulder injuries. Perhaps most importantly, tape tends to stretch over time. The initial taping of the injured shoulder places an undue restriction on mobility of the joint. Over a period of time, as the tape stretches and loosens, greater mobility is provided to the athlete at the expense of support to protect the injured shoulder. Finally, removing tape from an injury may be extremely painful to the athlete.

Another approach to stabilizing injured shoulder joints is the use of a removable shoulder brace, such as that disclosed in U.S. Pat. No. 5,735,198 issued to Sawa. Removable shoulder braces are typically directed to preventing abduction of the shoulder joint. For example, elastic straps are wrapped around the upper arm of the athlete and attached to the chest portion of the shoulder brace so as to restrict abduction of the arm. By restricting abduction of the arm, some prior shoulder braces could not be used by certain athletes, such as football receivers, linebackers, and defensive backs. Additionally, overly restrictive shoulder braces have been impractical for basketball and baseball players.

Most prior shoulder braces have been designed for treating specific types of injuries, such as anterior dislocations. Consequently, it is difficult or impossible to use these devices to treat other shoulder injuries. Additionally, a number of these shoulder devices are constructed of materials which slide or slip on the athlete's skin so that it is difficult to control rotational forces on the injured shoulder joint.

Applicant has previously received U.S. Pat. No. 5,628,725 which represented an improvement in the shoulder stabilizing art. Additionally, Applicant has also received U.S. Pat. No. 8,287,478 which represented a further improvement in the shoulder stabilizing art.

However, none of the prior art devices or Applicant's shoulder stabilizing systems or devices as set forth in U.S. Pat. Nos. 5,628,725 and 8,287,478 provided a shoulder stabilizing system or device which could provide 360 degrees of support utilizing four adjustable tensioning systems that were each responsible for a quadrant of the shoulder. Further, none of the prior art shoulder stabilizing systems or devices provided a system or device wherein a four tensioning system works together to give the user the ability to control all movements of the shoulder including internal and external rotation, horizontal abduction and adduction, while offering 360 degree support to the shoulder capsule.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A shoulder stabilizing system is disclosed which includes a flexible garment for positioning on the shoulder and upper body of a person. The garment includes a shoulder/sleeve portion, a chest portion, a back portion, a first mounting strap extending from the chest portion and a second mounting strap extending from the back portion. An adjustable first tensioning system interconnects the chest portion and the shoulder/sleeve portion. An adjustable second tensioning system interconnects the chest portion and the shoulder/sleeve portion. An adjustable third tensioning system interconnects the shoulder/sleeve portion and the back portion and a fourth tensioning system interconnects the shoulder/sleeve portion and the back portion.

The first, second, third and fourth tensioning systems function together to provide the person with the ability to control all movements of the shoulder including internal and external rotation, horizontal abduction and adduction, while providing 360 degrees support for the shoulder support capsule of the person.

In the preferred embodiment, each of the four tensioning systems are adjustable. In the preferred embodiment, each of the tensioning systems are dedicated to one quadrant of the shoulder.

It is therefore a principal object of the invention to provide an improved shoulder stabilizing system.

A further object of the invention is to provide a shoulder stabilizing system which includes four adjustable tensioning systems that are each responsible for a quadrant of the shoulder.

A further object of the invention is to provide a shoulder stabilizing system wherein the four tensioning systems thereof work together to give the user the ability to control all movements of the shoulder including internal and external rotation, horizontal abduction and adduction, while offering 360 degrees support to the shoulder capsule.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

Figure 1:
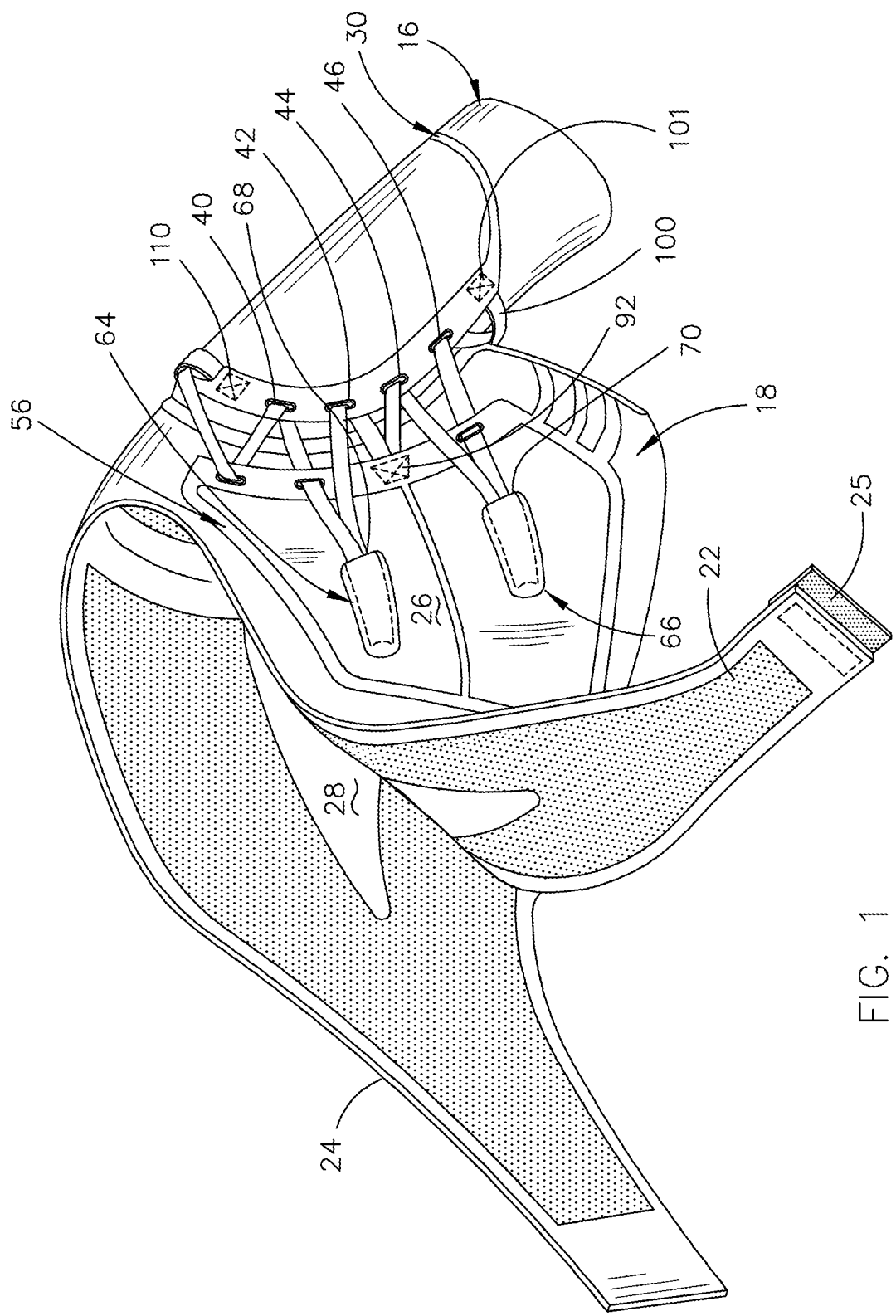
FIG. 1 is a frontal perspective view of the shoulder stabilizing system or device of the invention.
Figure 2:
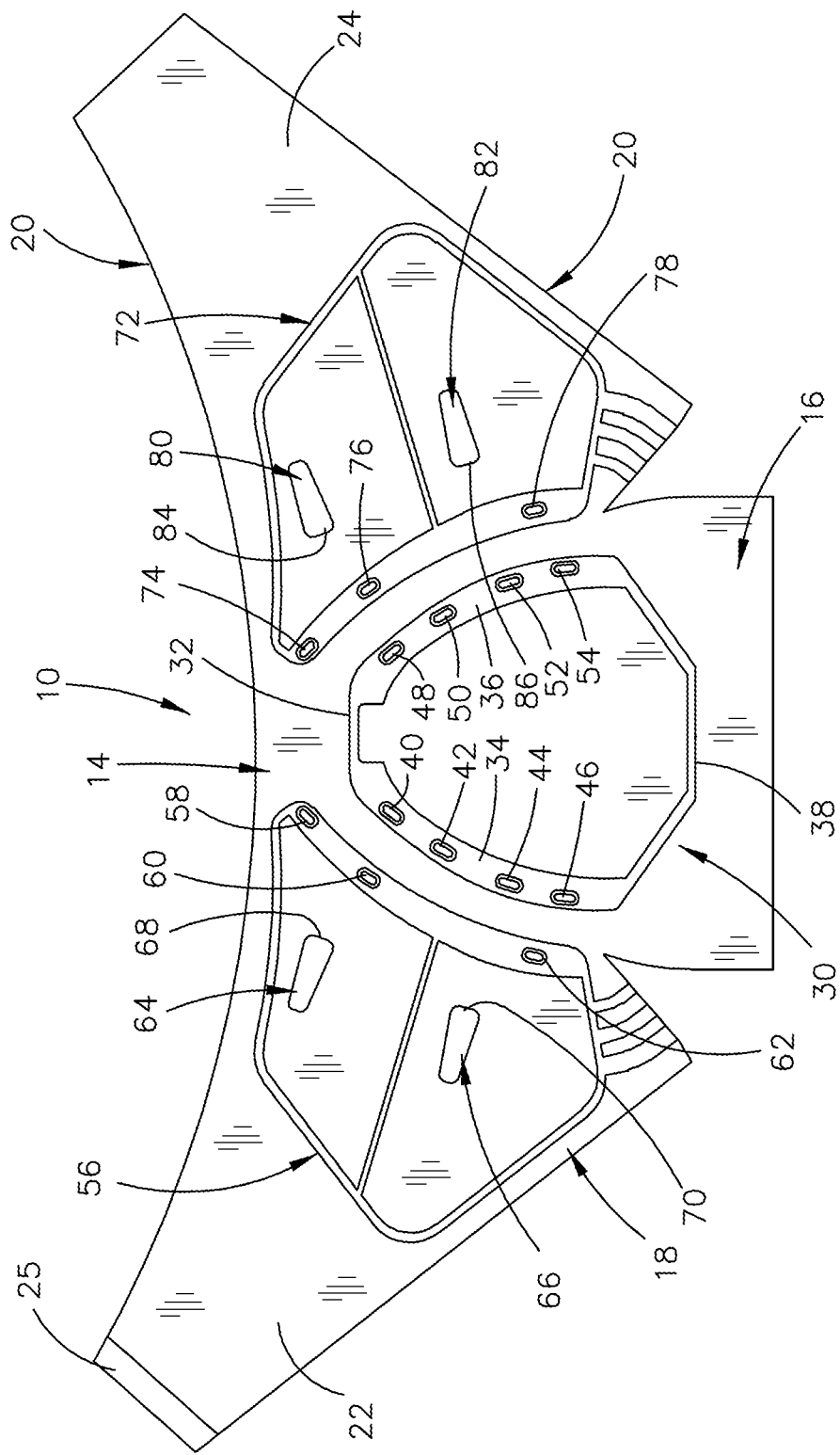
FIG. 2 is a plan view of the shoulder stabilizing system or device prior to the device being folded to create a sleeve portion and prior to the tensioning straps being secured thereto.
Figure 3:
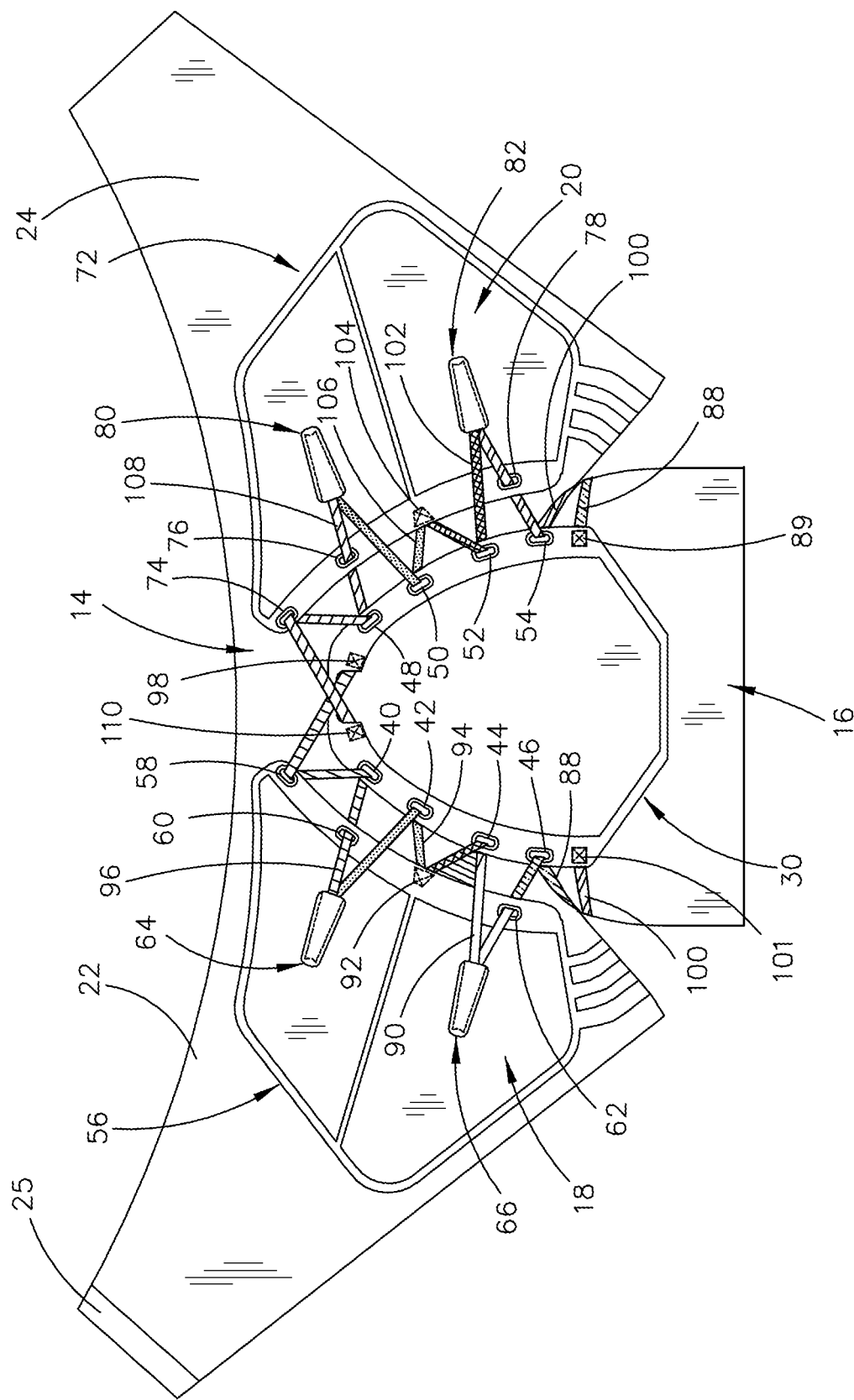
FIG. 3 is a view similar to FIG. 2 except that the tensioning straps have been secured thereto.
Figures 4, 5:
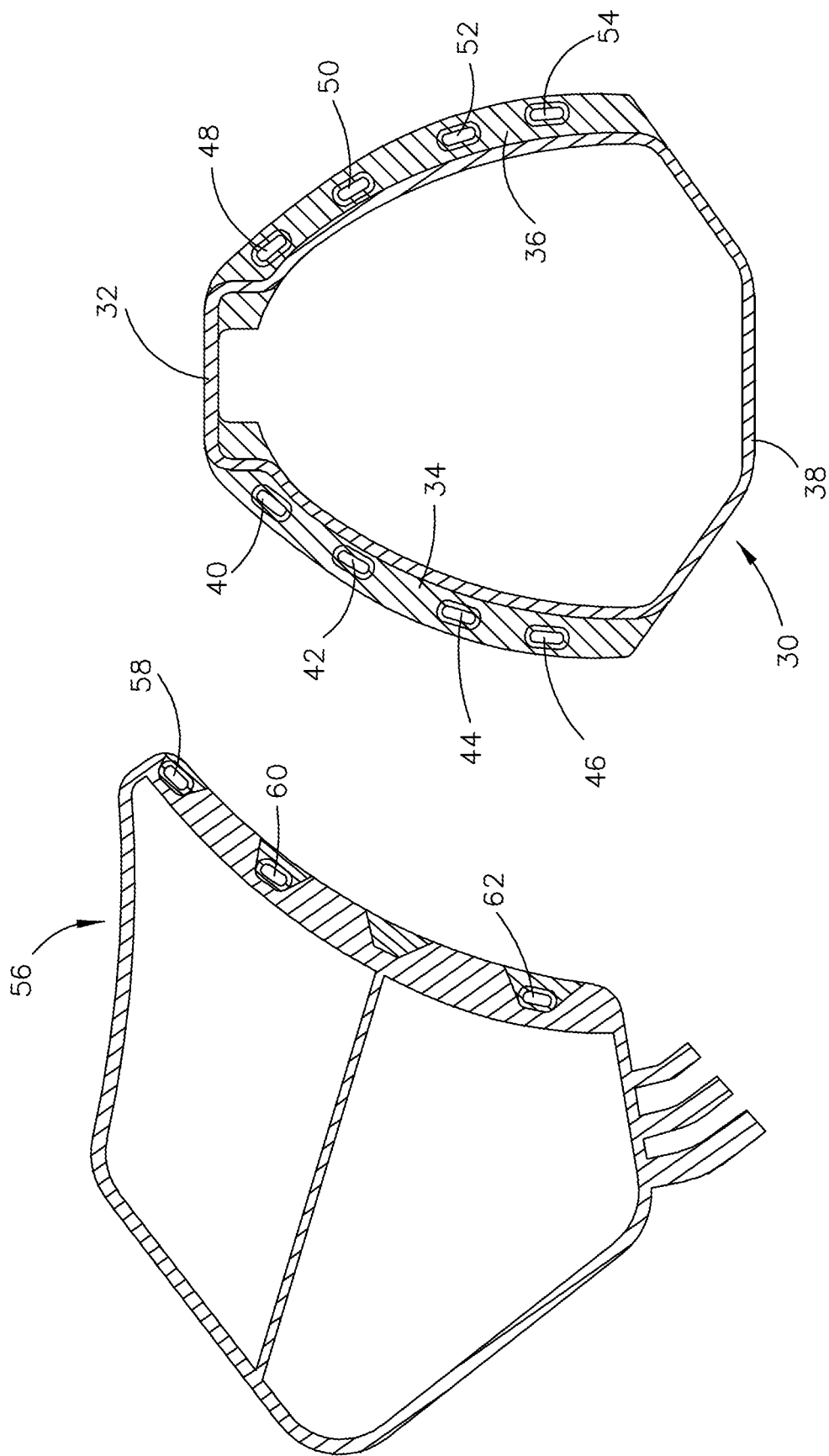
FIG. 4 is a sectional view of one of the strap supports of this invention.
FIG. 5 is a sectional view of another strap supports of the invention.
Figure 6:
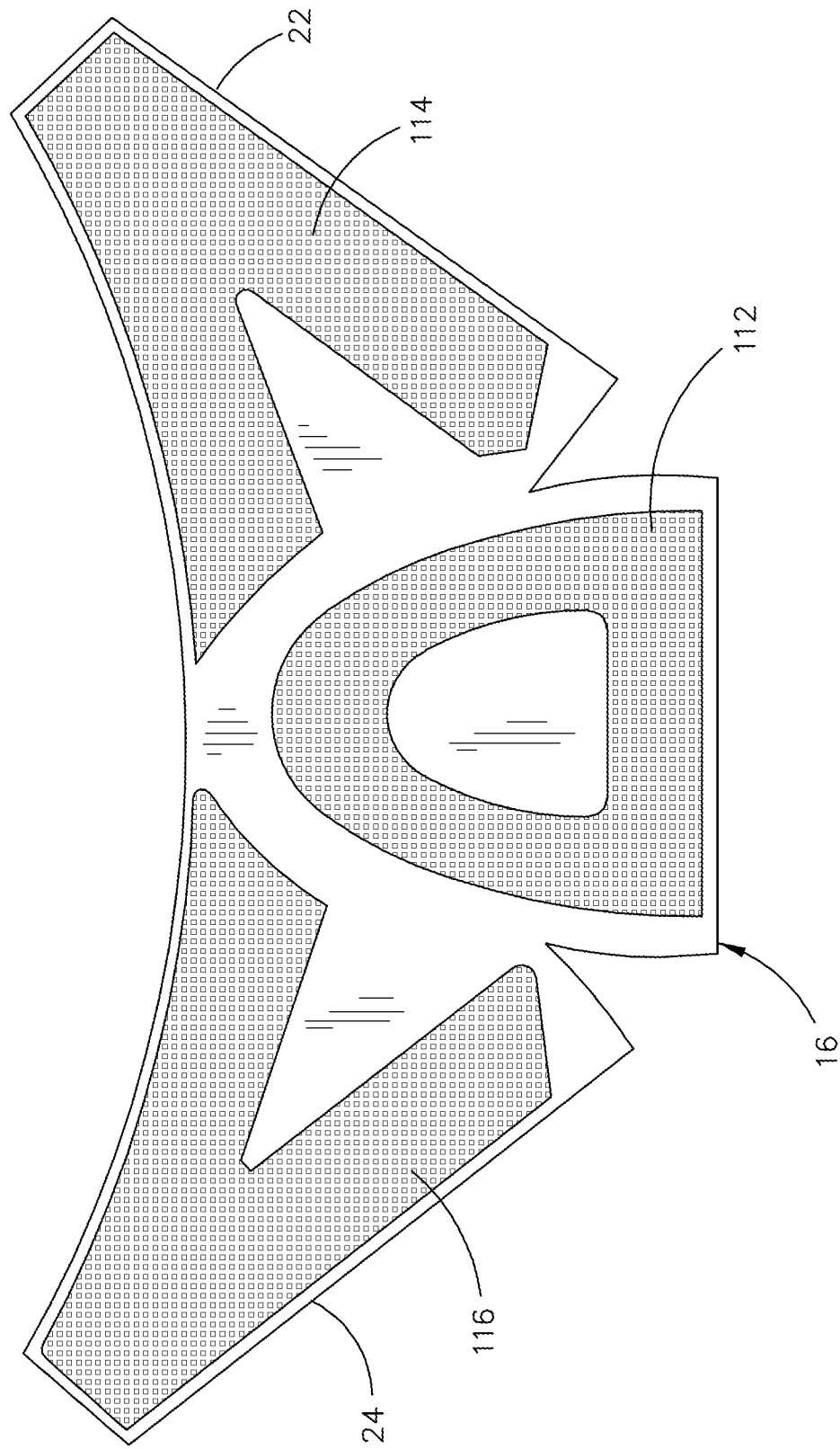
FIG. 6 is a plan view of the inner side of the device of this invention which illustrates rubberized non-slip segments secured to the inner side of the device of this invention.
Figure 7:
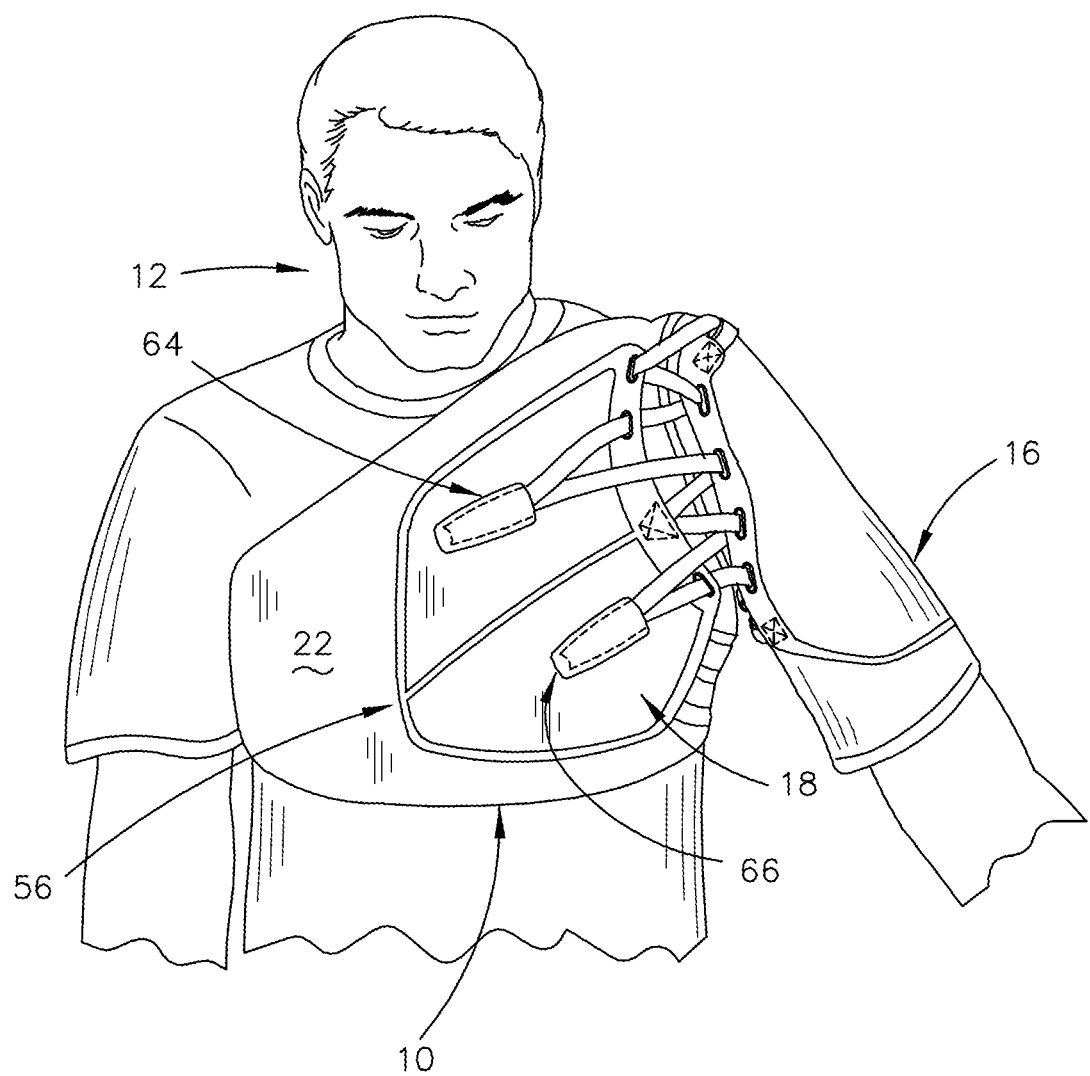
FIG. 7 is a partial frontal view of a user having a shoulder stabilizing system or device of this invention positioned on the left shoulder and body of the user.
Figure 8:
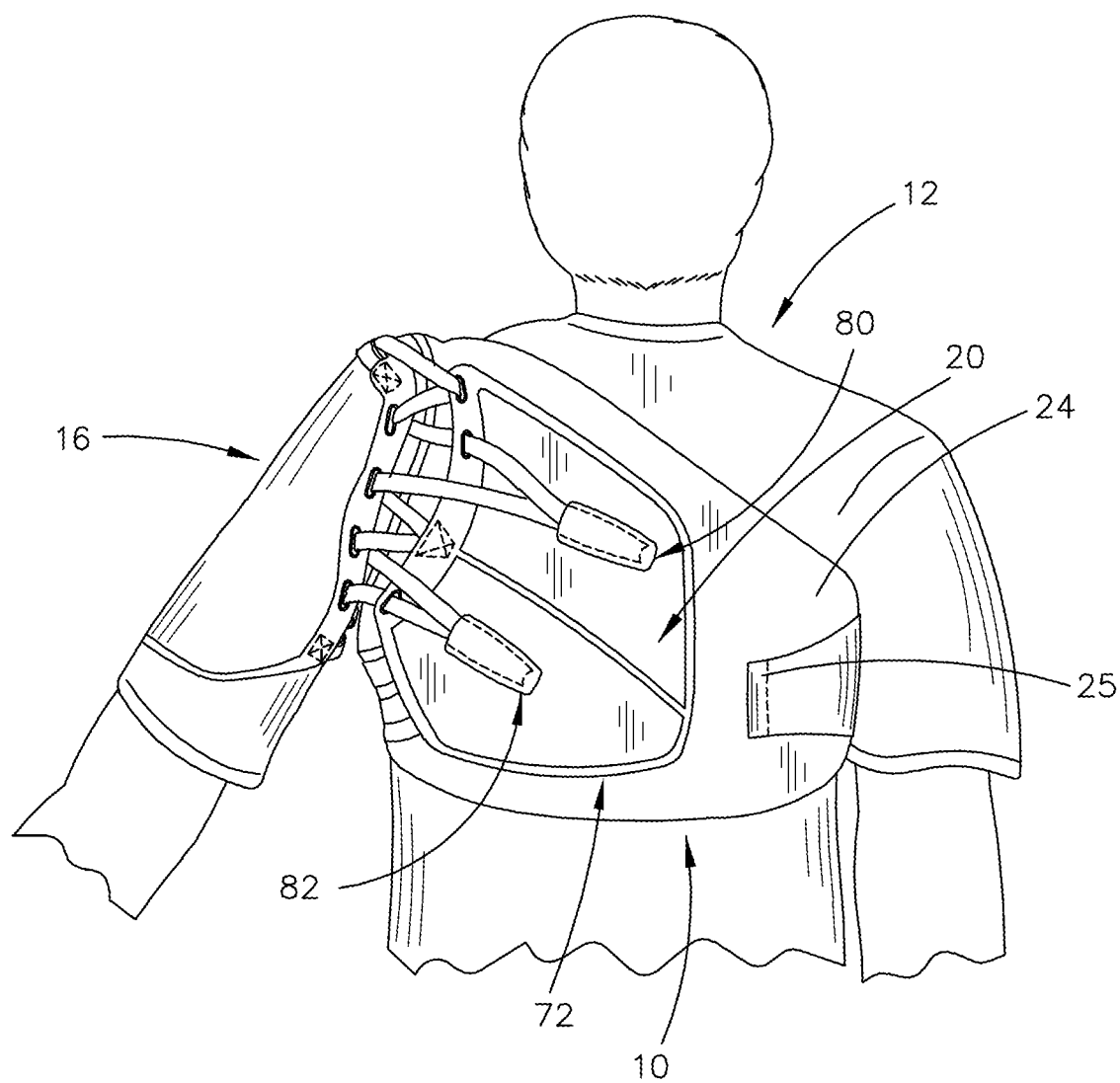
FIG. 8 is a partial back view of a user having the shoulder stabilizing system or device positioned on the left shoulder and body of the user.

The system of this invention is referred to by the reference numeral 10. The system 10 may be used on either the right or left shoulder of a person. The system illustrated herein will be described as being used with the left shoulder of a person 12. FIG. 2 illustrates the system prior it being folded and assembled. System 10 includes a shoulder portion 14, a sleeve portion 16, a chest portion 18, a back portion 20, a first strap portion 22 extending from chest portion 18 and a second strap portion 24 extending from said back portion 20. Shoulder portion 14, sleeve portion 16, chest portion 18, back portion 20, strap portion 22 of strap portion 24 are comprised of a flexible material such as Neoprene which has an exterior side 26 and an interior side 28. The exterior side 26 of those portions is of loop construction such as the loop fastener of a hook and loop fastener, such as Velcro®.

Shoulder portion 14 and sleeve portion 16 have a non-stretchable rubber support member 30 secured to the exterior sides thereof by sonic welding. Support member 30 includes an upper member 32, a front member 34, a back member 36 and a lower member 38. Front member 34 has spaced-apart slot-like openings 40, 42, 44 and 46 formed therein. Back member 36 has slot-like openings 48, 50, 52 and 54 formed therein.

A non-stretchable support member 56 is secured to the exterior side of chest portion 18 by ultra-sonic welding and has slot-like openings 58, 60 and 62 formed therein. A pair of pockets 64 and 66 are secured to the exterior of chest portion 18 by stitching. Pockets 64 and 66 have open ends 68 and 70 respectively. Back portion 20 has a non-stretchable rubber support member 72 secured to the exterior thereof. Support member 72 has slot-like openings 74, 76 and 78 formed therein. Support member 72 has a pair of pockets 80 and 82 secured thereto and which have open ends 84 and 86 respectively. The pockets 80 and 82 have hook fasteners at the inner sides thereof which permit the pockets 80 and 82 to be adjustably secured to the loops on the exterior of back portion 20.

A strap 88 has one end thereof secured to support member 30 at 89. Strap 88 extends through opening 46 in support member 30 and has its other end received in and secured to pocket 66. A strap 90 has one end thereof received in and secured to pocket 66. Strap 90 extends through opening 44 in support member 36 and has its other end secured to support member 36 at 92. Strap 94 has one end thereof secured to support member 36 at 92. Strap 94 extends through opening 42 in support member 30 and has its other end received in pocket 64 and secured thereto. Strap 96 has one end received in pocket 64 and is secured thereto. Strap 96 extends from pocket 64 through opening 60 in support member 36 and through opening 40 in support member 30. Strap 96 then extends through opening 58 in support member 36. The other end of strap 96 is secured to support member 30 at 98.

Strap 100 has one end secured to support member 30 and extends through opening 54 in support member 30. The other end of strap 100 is received in and is secured to pocket 82. Strap 102 has one end received in pocket 82 and is secured thereto. Strap 102 extends from pocket 82 and extends through opening 52 in support member 30. The other end of strap 102 is secured to support member 72 at 104. One end of strap 106 is secured to support member 72 at 104 and extends through opening 50 in support member 30. Strap 106 has its other end received by pocket 80 and is secured thereto. A strap 108 has one end received in pocket 80 and is secured thereto. Strap 108 extends through opening 74 in support member 72 and through opening 48 in support 30. Strap 108 then extends through opening 74 in support member 72. The other end of strap 108 is secured to support member 30 at 110. Straps 88, 90, 94, 96, 100, 102, 106 and 108 are formed of a stretchable material such as polyurethane.

In operation, the shoulder stabilizing system of this invention is positioned on either the right or left shoulder and upper body of a person. The chest portion of the system is positioned at the front of the person's chest. The shoulder/sleeve portion of the garment extends over the shoulder and permits the person to extend his or her arm through the sleeve portion. The garment also includes a back portion which extends rearwardly from the rearward end of the shoulder/sleeve portion so as to be positioned at the back side of the person's shoulder.

The four tensioning systems described above are each dedicated to one quadrant of the four quadrants of the shoulder. The tensioning systems resist certain movements of the person's shoulder and, as the person reaches the limits of movement, the tensioning system increases the resistance to such movement. The first two tensioning systems interconnect the upper and lower portions of the chest portion with the upper forward and lower forward ends of the shoulder/sleeve portion. The third tensioning system interconnects the rearward end of the shoulder/sleeve portion with the upper end of the back portion. The fourth tensioning system interconnects the lower end of the shoulder/sleeve portion with the lower forward end of the back portion.

The shoulder stabilizing system 10 of this invention provides 360 degrees of support utilizing the four adjustable tensioning systems mentioned above with each of those systems being responsible for a quadrant of the shoulder. The four tensioning systems work together to give the user the ability to control all movements of the shoulder including internal and external rotation, horizontal abduction and adduction, while offering 360 degrees support to the shoulder capsule. The non-stretchable rubber support members 30, 56 and 72 limit the amount of stretch in the material. The support members 30, 56 and 72 also function to form an external joint of the device.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A shoulder stabilizing system, comprising:
a garment for positioning on the shoulder and an upper body of a person;
said garment including a shoulder/sleeve portion, a chest portion, a back portion, a first strap portion extending from said chest portion and a second strap portion extending from said back portion;
said first and second strap portions being configured to be selectively adjustably secured together;
said garment being comprised of a flexible material having an exterior side and an interior side;
said exterior side of said garment having loop fasteners thereon;
said chest portion having an inner end, an outer end, an upper end, a lower end, an exterior side and an interior side;
said inner side of said chest portion having first, second and third spaced-apart strap openings formed therein;
said shoulder/sleeve portion having an upper end, a lower end, a forward end and a rearward end;
said forward end of said shoulder/sleeve portion having first, second, third and fourth spaced-apart strap openings formed therein;
said rearward end of said shoulder/sleeve portion having fifth, sixth, seventh and eighth spaced-apart strap openings formed therein;
said back portion having an upper end, a lower end, an outer end and an inner end;
said outer end of said back portion having first, second and third spaced-apart strap openings formed therein;
an elongated first strap having first and second ends;
said first end of said first strap being secured to said rearward end of said shoulder/sleeve portion above said lower end thereof and thence extending through said first strap opening in said shoulder/sleeve portion and thence extending through said first strap opening in said chest portion and thence extending to said chest portion whereby said second end of first strap is positioned at the exterior side of said chest portion at a first location;
an elongated second strap having first and second ends;
said first end of said second strap being positioned adjacent to said second end of said first strap at said first location;
said second end of said first strap and said first end of said second strap being selectively adjustably secured to said chest portion at said first location;
said second strap extending from said first location through said second strap opening in said shoulder/sleeve portion and thence extending to a first attachment location on said chest portion wherein said second end of said second strap is fixed;
an elongated third strap having first and second ends;
said first end of said third strap being fixedly secured to said chest portion at said first attachment location on said chest portion and thence extending through said third strap opening in said shoulder/sleeve portion and thence extending to said chest portion whereby said second end of said third strap is positioned at the exterior side of said chest portion at a second location which is spaced from said first location;
an elongated fourth strap having first and second ends;
said first end of said fourth strap being positioned adjacent said second end of said third strap at said second location;
said fourth strap extending from said second location through said second strap opening of said chest portion, thence through said fourth strap opening in said shoulder/sleeve portion, and thence through said third strap opening in said chest portion and thence to said shoulder/sleeve portion wherein it is fixed thereto at said upper end of said shoulder/sleeve portion at said rearward end thereof;
an elongated fifth strap having first and second ends;
said first end of said fifth strap being secured to said forward end of said shoulder/sleeve portion above said lower end thereof and thence extending through said fifth strap opening in said shoulder/sleeve portion and thence through said first strap opening in said back portion whereby said second end of said fifth strap is positioned at the exterior side of said back portion at a third location;
an elongated sixth strap having first and second ends;
said first end of said sixth strap being positioned adjacent to said second end of said fifth strap at said third location;
said sixth strap extending from said third location through said sixth strap opening in said shoulder/sleeve portion and thence extending to a first attachment location on said back portion wherein said second end of said sixth strap is fixed;
an elongated seventh strap having first and second ends;
said first end of said seventh strap being fixedly secured to said back portion at said first attachment location of said back portion and thence extending through said seventh strap opening in said back portion and thence to a fourth location on said back portion;
an elongated eighth strap having first and second ends;
said first end of said eighth strap being positioned adjacent said second end of said seventh strap at said fourth location;
said eighth strap extending from said fourth location through said third strap opening in said back portion, thence through said eighth strap opening in said shoulder/sleeve portion, thence through said fourth strap opening in said back portion, and thence to said forward end of said shoulder/sleeve portion at the said upper end thereof;
said second end of said third strap and said first end of said fourth strap being selectively adjustably secured to said chest portion at said second location on said chest portion;
said second end of said fifth strap at said second end of said sixth strap being selectively adjustably secured to said back portion at said third location; and
said second end of said seventh strap at said first end of said eighth strap being selectively adjustably secured to said back portion at said fourth location.

2. The shoulder stabilizing system of claim 1 wherein said first, second, third, fourth, fifth, sixth, seventh and eighth straps are comprised of a stretchable material.

3. The shoulder stabilizing system of claim 1 wherein said exterior side of said chest portion has a first support member secured thereto which has an inner end in which said first, second, third and fourth strap openings are formed therein, and wherein said exterior side of said shoulder/sleeve portion has a second support member secured thereto which has forward and rearward ends with said forward end of said second support having said first, second, third and fourth strap openings formed therein, and wherein said rearward end of said second support member has said fifth, sixth, seventh and eighth strap openings formed therein and wherein back portion has a third support member secured to said exterior side thereof and which has an inner end which has said fifth, sixth, seventh and eighth strap openings formed therein.

4. The shoulder stabilizing system of claim 3 wherein said first, second and third supports are non-stretchable.

5. The shoulder stabilizing system of claim 4 wherein said garment is comprised of a stretchable material.

6. The shoulder stabilizing system of claim 1 wherein at least a portion of the interior side of said garment has a rubber material positioned thereon.

7. A shoulder stabilizing system, comprising:
a garment for positioning on the shoulder and an upper body of a person;
said garment including a shoulder/sleeve portion, a chest portion, a back portion, a first strap portion extending from said chest portion and a second strap portion extending from said back portion;
said first and second strap portions being configured to be selectively adjustably secured together;
said garment being comprised of a flexible material having an exterior side and an interior side;
said exterior side of said garment having loop fasteners thereon;
said chest portion having an inner end, an outer end, an upper end, a lower end, an exterior side and an interior side;
said inner end of said chest portion having first, second and third spaced-apart strap openings formed therein;
a non-stretchable first support member secured to said exterior side of said chest portion;
said first support member having an inner end, an outer end, an upper end, and a lower end;
said inner end of said first support member having first, second and third spaced-apart strap openings formed therein which register with said first, second and third strap openings in said inner end of said chest portion;
said shoulder/sleeve portion having an upper end, a lower end, a forward end, a rearward end; an exterior side and an interior side;
said forward end of said shoulder/sleeve portion having first, second, third and fourth spaced-apart strap openings formed therein;
said rearward end of said shoulder/sleeve portion having fifth, sixth, seventh and eighth spaced-apart strap openings formed therein;
a non-stretchable second support member secured to said exterior side of said shoulder/sleeve portion;
said second support member having an upper end, a lower end, a forward end and a rearward end;
said forward end of said second support member having first, second, third and fourth spaced-apart strap openings formed therein which register with said first, second, third and fourth strap openings in said forward end of said shoulder/sleeve portion;
said rearward end of said second support member having fifth, sixth, seventh and eighth strap openings formed therein which register with said fifth, sixth, seventh and eighth strap openings in said rearward end of said shoulder/sleeve portion;
said back portion having an upper end, a lower end, an outer end, an inner end, an exterior side and an interior side;
said outer end of said back portion having first, second and third spaced-apart strap openings formed therein;
a non-stretchable third support member secured to said exterior side of said back portion;
said third support having an upper end, a lower end, an outer end and an inner end;
said outer end of said third support member having first, second and third strap openings formed therein which register with said first, second and third strap openings formed in said outer end of said back portion;
an elongated first strap having first and second ends;
said first end of said first strap being secured to said rearward end of said shoulder/sleeve portion above said lower end thereof and thence extending through said first strap opening in said shoulder/sleeve portion and thence extending through said first strap opening in said chest portion and thence extending to said chest portion whereby said second end of first strap is positioned at the exterior side of said chest portion at a first location;
an elongated second strap having first and second ends;
said first end of said second strap being positioned adjacent to said second end of said first strap at said first location;
said second end of said first strap and said first end of said second strap being selectively adjustably secured to said chest portion at said first location;
said second strap extending from said first location through said second strap opening in said shoulder/sleeve portion and thence extending to a first attachment location on said chest portion wherein said second end of said second strap is fixed;
an elongated third strap having first and second ends;
said first end of said third strap being fixedly secured to said chest portion at said first attachment location on said chest portion and thence extending through said third strap opening in said shoulder/sleeve portion and thence extending to said chest portion whereby said second end of said third strap is positioned at the exterior side of said chest portion at a second location which is spaced from said first location;
an elongated fourth strap having first and second ends;
said first end of said fourth strap being positioned adjacent said second end of said third strap at said second location;
said fourth strap extending from said second location through said second strap opening of said chest portion, thence through said fourth strap opening in said shoulder/sleeve portion, and thence through said third strap opening in said chest portion and thence to said shoulder/sleeve portion wherein it is fixed thereto at said upper end of said shoulder/sleeve portion at said rearward end thereof;
an elongated fifth strap having first and second ends;
said first end of said fifth strap being secured to said forward end of said shoulder/sleeve portion above said lower end thereof and thence extending through said fifth strap opening in said shoulder/sleeve portion and thence through said first strap opening in said back portion whereby said second end of said fifth strap is positioned at the exterior side of said back portion at a third location;

an elongated sixth strap having first and second ends;

said first end of said sixth strap being positioned adjacent to said second end of said fifth strap at said third location;

said sixth strap extending from said third location through said sixth strap opening in said shoulder/sleeve portion and thence extending to a first attachment location on said back portion wherein said second end of said sixth strap is fixed;

an elongated seventh strap having first and second ends;

said first end of said seventh strap being fixedly secured to said back portion at said first attachment location of said back portion and thence extending through said seventh strap opening in said back portion and thence to a fourth location on said back portion;

an elongated eighth strap having first and second ends;

said first end of said eighth strap being positioned adjacent said second end of said seventh strap at said fourth location;

said eighth strap extending from said fourth location through said third strap opening in said back portion, thence through said eighth strap opening in said shoulder/sleeve portion, thence through said fourth strap opening in said back portion, and thence to said forward end of said shoulder/sleeve portion at the said upper end thereof;

said second end of said third strap and said first end of said fourth strap being selectively adjustably secured to said chest portion at said second location on said chest portion;

said second end of said fifth strap at said second end of said sixth strap being selectively adjustably secured to said back portion at said third location; and said second end of said seventh strap at said first end of said eighth strap being selectively adjustably secured to said back portion at said fourth location.

8. The shoulder stabilizing system of claim 7 wherein said first, second, third, fourth, fifth, sixth, seventh and eighth straps are comprised of a stretchable material.

9. The shoulder stabilizing system of claim 7 wherein said garment is comprised of a stretchable material.

10. The shoulder stabilizing system of claim 7 wherein at least a portion of the interior side of said garment has a rubber material positioned thereon.

* * * * *